(12) United States Patent
Green

(10) Patent No.: US 8,642,054 B2
(45) Date of Patent: Feb. 4, 2014

(54) STERILANT SYSTEM

(75) Inventor: Bruce Philip Green, Northampton (GB)

(73) Assignee: Tristel PLC, Snailwell, Cambridgeshire (GB)

(*) Notice: Subject to any disclaimer, the term of this patent is extended or adjusted under 35 U.S.C. 154(b) by 582 days.

(21) Appl. No.: 10/935,651

(22) Filed: Sep. 7, 2004

(65) Prior Publication Data

US 2006/0051387 A1 Mar. 9, 2006

(51) Int. Cl.
*A61K 8/02* (2006.01)
*A61L 2/08* (2006.01)

(52) U.S. Cl.
USPC .............................. 424/401; 424/414; 422/28

(58) Field of Classification Search
None
See application file for complete search history.

(56) References Cited

U.S. PATENT DOCUMENTS

| | | | |
|---|---|---|---|
| 2,833,624 A | 5/1958 | Sprauer | |
| 3,568,627 A | 3/1971 | Selinger et al. | |
| 3,933,274 A | 1/1976 | Emmons et al. | |
| 4,013,761 A | 3/1977 | Ward et al. | |
| 4,330,531 A | 5/1982 | Alliger | |
| 4,345,716 A | 8/1982 | Armstrong et al. | |
| 4,361,235 A | 11/1982 | Gautier | |
| 4,438,871 A | 3/1984 | Eckert | |
| RE31,779 E | 12/1984 | Alliger | |
| 4,516,726 A | 5/1985 | Hoie | |
| 4,534,952 A | 8/1985 | Rapson et al. | |
| 4,538,919 A | 9/1985 | Bohnensieker | |
| 4,646,973 A * | 3/1987 | Focaracci | 239/428.5 |
| 4,689,215 A | 8/1987 | Ratcliff | |
| 4,705,461 A | 11/1987 | Clements | |
| 4,789,100 A | 12/1988 | Senf | |
| 4,789,166 A | 12/1988 | Rericha et al. | |
| 4,806,079 A | 2/1989 | Kuhn | |
| 4,832,580 A | 5/1989 | Tsuyoshi et al. | |
| 4,854,501 A | 8/1989 | Ricci | |
| 4,876,023 A | 10/1989 | Dickenson et al. | |
| 4,891,216 A * | 1/1990 | Kross et al. | 424/661 |
| 4,906,488 A | 3/1990 | Pera | |
| 4,940,701 A | 7/1990 | Davis | |
| 4,978,530 A | 12/1990 | Strong | |
| 5,002,204 A | 3/1991 | Sakai | |
| 5,091,107 A * | 2/1992 | Hutchings | 252/187.21 |
| 5,133,483 A | 7/1992 | Buckles | |
| 5,141,803 A * | 8/1992 | Pregozen | 442/123 |
| 5,146,944 A | 9/1992 | Waldrum | |
| 5,152,461 A | 10/1992 | Proctor | |
| 5,197,636 A | 3/1993 | Mitchell et al. | |
| 5,204,081 A | 4/1993 | Mason et al. | |
| 5,213,884 A | 5/1993 | Fellows | |
| 5,224,627 A | 7/1993 | Weag | |
| 5,227,168 A | 7/1993 | Chvapil et al. | |
| 5,337,929 A | 8/1994 | Van Der Heijden | |
| 5,388,761 A | 2/1995 | Langeman | |
| 5,425,815 A | 6/1995 | Parker et al. | |
| 5,518,675 A | 5/1996 | Sims | |
| 5,524,983 A | 6/1996 | Dittgen et al. | |
| 5,647,506 A * | 7/1997 | Julius | 221/46 |
| 5,649,647 A | 7/1997 | Kodarar | |
| 5,673,821 A | 10/1997 | Davis et al. | |
| 5,696,046 A | 12/1997 | Green | |
| 5,702,992 A | 12/1997 | Martin et al. | |
| 5,721,521 A | 2/1998 | Drabeck et al. | |
| 5,738,840 A | 4/1998 | Richter | |
| 5,766,333 A | 6/1998 | Lukens | |
| 5,783,146 A | 7/1998 | Williams, Jr. | |
| 5,895,638 A | 4/1999 | Tenney | |
| 5,958,536 A | 9/1999 | Gelsinger et al. | |
| 5,985,302 A | 11/1999 | Dorr et al. | |
| 6,007,772 A | 12/1999 | Green | |
| 6,013,614 A | 1/2000 | Mahdessian | |
| 6,082,534 A | 7/2000 | Dotson | |
| 6,399,557 B2 | 6/2002 | Perkins et al. | |
| 6,431,189 B1 | 8/2002 | Deibert | |
| 6,484,879 B2 | 11/2002 | Desmarais et al. | |
| 6,566,318 B2 | 5/2003 | Perkins et al. | |
| 6,624,130 B2 | 9/2003 | Giblin et al. | |
| 6,651,848 B1 | 11/2003 | Redmond | |
| 6,669,387 B2 | 12/2003 | Gruenbacher et al. | |
| 6,696,047 B2 | 2/2004 | Scott et al. | |
| 6,753,306 B2 | 6/2004 | Simpson | |
| 2002/0006887 A1 | 1/2002 | Radwanski et al. | |
| 2003/0068454 A1 | 4/2003 | Smith | |
| 2003/0180247 A1 * | 9/2003 | Morelli et al. | 424/70.24 |
| 2003/0216281 A1 | 11/2003 | DeLeo et al. | |
| 2004/0109853 A1 | 6/2004 | McDaniel | |
| 2004/0195824 A1 | 10/2004 | Blank | |
| 2005/0159063 A1 | 7/2005 | Hill et al. | |
| 2005/0210615 A1 * | 9/2005 | Shastry et al. | 15/210.1 |

FOREIGN PATENT DOCUMENTS

| | | |
|---|---|---|
| DE | 37 14 699 | 1/1988 |
| DE | 41 34 494 | 4/1993 |

(Continued)

OTHER PUBLICATIONS

Abstract for JP 60 58147. Apr. 4, 1985.

(Continued)

*Primary Examiner* — Kyle Purdy

(74) *Attorney, Agent, or Firm* — Merchant & Gould P.C.

(57) ABSTRACT

A two-part sterilant system comprises a first part comprising a first reagent in a carrier medium and a second part which is miscible with the first part and which comprises a second reagent in a carrier medium. The first reagent and the second reagent will react when mixed to provide a sterilizing composition. The first part is contained in a pump dispenser (2) whereby it may be dispensed as a fluid, and the second part is absorbed or impregnated in at least one fabric member (18) in a sealed container (20).

24 Claims, 4 Drawing Sheets

(56) References Cited

FOREIGN PATENT DOCUMENTS

| | | |
|---|---|---|
| EP | 0 017 968 | 4/1980 |
| EP | 0 081 017 | 6/1983 |
| EP | 0 423 817 A2 | 10/1990 |
| EP | 0 423 816 | 4/1991 |
| EP | 0 423 817 | 4/1991 |
| EP | 0 314 994 | 10/1998 |
| EP | 1 310 263 | 9/2001 |
| EP | 0 785 719 | 1/2003 |
| EP | 1 340 511 | 9/2003 |
| FR | 2 569 779 | 3/1986 |
| GB | 2 004 475 | 4/1979 |
| GB | 2 304 706 | 3/1997 |
| GB | 2 329 589 | 3/1999 |
| JP | 2001 129041 | 5/2001 |
| WO | WO 96/10916 | 4/1996 |
| WO | WO 00/56203 | 9/2000 |
| WO | WO 00/76916 | 12/2000 |
| WO | WO 01/37886 | 5/2001 |
| WO | WO 01/64325 | 9/2001 |
| WO | WO 03/000586 | 1/2003 |

OTHER PUBLICATIONS

Abstract for JP 7 1828. Jan. 20, 1995.
Rostker, B., "Case narrative: Possible chemical warfare agent incident involving a United States Marine (Last update Mar. 16, 2000)." http://www.gulflink.osd.mil/injured_marine/index.htm.
Beeby et al., "A bacterial spore test piece for the control of ethylene oxide sterilization," *J. Appl. Bact.* (1965) 28 (3): 349-360.
Office Action for co-pending U.S. Appl. No. 10/935,030 mailed Aug. 31, 2009.
Hooper, P., "Decontamination—Machinery and Testing," *ISSM Journal* (2000) 5 (1): 4-8.
"Washer-disinfectors—Validation and verification," *Health Technical Memorandum 2030* (1997): 1-163.

* cited by examiner

STERILANT SYSTEM

FIELD OF THE INVENTION

The present invention relates to a two-part sterilant system, notably to a system for producing chlorine dioxide ($ClO_2$). The invention is particularly for use in sterilising medical supplies and equipment, but it is not limited to these uses.

BACKGROUND TO THE INVENTION

Two-part sterilising solutions are used in applications where the active sterilising ingredient is unstable over time. The solution is therefore prepared in situ shortly before it is to be used. A particularly important sterilising agent is chlorine dioxide, which may be formed from mixtures of various reagents including: chlorite and acid; chlorate, peroxide and acid; and chlorite, hypochlorite, and a suitable buffer. Chlorine dioxide has excellent sterilising and bactericidal properties, and oral ingestion in man and animals has been shown to be relatively safe.

The cleaning of endoscopes and other medical equipment with suitable chlorine dioxide solutions is known from earlier patents in the name of the present inventor, for example, European Patent Number 0 785 719 and U.S. Pat. Nos. 5,696, 046 and 6,007,772, the contents of which are hereby incorporated by reference.

It is not always convenient to mix up batches of solutions for use in sterilising equipment. For wiping down (rather than thoroughly cleaning inside and out) of endoscopes and probes, wipes of alcohol, general-purpose detergent, or soapy water are generally used, but these are not as effective as chlorine dioxide. It is desirable to be able readily to make up small quantities of two-component sterilising agents when desired and to be able to make such agents up in a form in which they may be readily handled for a particular application.

SUMMARY OF THE INVENTION

According to a first aspect of the present invention there is provided a two-part sterilant system comprising:
(a) a first part comprising a first reagent in a carrier medium; and
(b) a second part which is miscible with the first part and which comprises a second reagent in a carrier medium;
wherein the first reagent and the second reagent will react when mixed to provide a sterilising composition;
characterised in that the first part is contained in a pump dispenser whereby it may be dispensed as a fluid, and in that the second part is absorbed or impregnated in at least one fabric member in a sealed container.

The term "fluid" is used herein to include liquids, foams, sprays, pastes, aerosols, powders, sols and gels. It is particularly preferred that the first part is dispensed as a foam or a spray to facilitate its coverage of a desired area of the fabric member. Optionally, the dispenser may have a relatively large dispensing head, for supplying the fluid over all or a substantial part of a surface of the fabric member. For example, the dispensing head may take the form of a rose or sprinkler with a multitude of small orifices to spread the fluid over the fabric member.

The pump dispenser is preferably a trigger-operated dispenser, both for convenience and to facilitate the dispensing of metered quantities. However, other pump dispensers could be used, for example, a squeeze bottle with a suitable spray or foam nozzle. The invention will, for convenience, be described hereinafter with reference to the use of a trigger-operated dispenser, but it is to be understood that it is not limited to this embodiment.

By putting up the first part in a trigger-operated dispenser, small quantities may be readily dispensed without risk of spillage. Preferably the dispenser comprises a sprayer apparatus that provides the first part as a foam so that it is at least partly form-retaining and can be readily seen and manipulated. We have also found that providing the first part in a foam may have the beneficial effect of reducing the odour of chlorine dioxide when the wipe is activated. The invention will for convenience be described with reference to this preferred embodiment, but it will be understood that the invention is not limited to this embodiment.

The trigger sprayer may include a mixing chamber to facilitate mixing of the first part with air, for example as described in U.S. Pat. No. 5,337,929.

The fabric members may be formed from any suitable fabrics, either woven or non-woven. They may be of natural or man-made fibres, for example polyester, cotton, cellulose or mixtures thereof. Other suitable fabrics will be well known to those skilled in the textile or fabric arts.

The fabric member may comprise a fabric wipe or cloth, or a gauze, pad, or other wound dressing material. Once prepared, the fabric member will have biocidal properties and may be used to dress wounds, ulcers, or the like while promoting a sterile local environment around the wound. For convenience, the invention will be described hereinafter with reference to the use of a fabric wipe, but it is to be understood that the invention is not limited to this embodiment.

By providing the second part absorbed in a fabric wipe, a sterilising wipe may readily be prepared by applying the first part to the wipe. The user may fold the wipe or rub two halves together to facilitate mixing. The wipes are particularly useful for cleaning, disinfecting, and sterilising surfaces and equipment, notably in a medical environment.

The first part may include a coloured component so that a visual indication of the coverage of the wipe with the first part can be made.

In a preferred embodiment, at least one of the first and second parts is provided with an indicator reagent that changes colour to show that sufficient mixing has taken place. Where the first part and the second part are of different pH, the indicator may be a pH-sensitive indicator. Suitable indicators are well known to those skilled in the art, non-limiting examples including: phenol red, litmus, thymol blue, pentamethoxy red, tropeolin OO, 2,4-dinitrophenol, methyl yellow, methyl orange, bromophenol blue, tetrabromophenol blue, alizarin sodium sulphonate, α-naphthyl red, p-ethoxychrysoidine, bromocresol green, methyl red, bromocresol purple, chlorophenyl red, bromothymol blue, p-nitrophenol, azolitmin, neutral red, rosalic acid, cresol red, α-naphtholphthalein, tropeolin OOO, phenolphthalein, α-naphtholbenzein, thymolphthalein, nile blue, alizarin yellow, diazo violet, tropeolin O, nitramine, Poirrer's blue, trinitrobenzoic acid, and mixtures thereof. It is preferred that the indicator is selected so that both parts are separately colourless and the colour develops when the two parts are mixed.

Alternatively, or additionally, one or more fluorescent additives may be included so that the mixture fluoresces to indicate mixing. Non-limiting examples of suitable fluorescing agents include: 4-methylumbelliferone, 3,6-dihydroxanthone, quinine, thioflavin, 1-napthol, harmine, coumarin, acridine orange, cotarmine, and mixtures thereof.

The indicator (colour change or fluorescent) may be included in either part. Preferred proportions by weight are about 0.1 to 10%, notably about 0.5 to 2%.

The carrier mediums may be fluids such as liquids or sols, or they may be more form-retaining or viscous compositions such as gels or pastes. It is preferred that at least one reagent is present in an aqueous fluid, although other additives may of course be present. Preferably both reagents are put up in aqueous fluids.

The trigger-operated dispenser may be a conventional atomiser or foamer, or other manual pump in which the contents are expelled manually by operation of the trigger by the user. Alternatively, the dispenser may contain a propellant to dispense the contents when operation of the trigger opens a valve, as is well known in applications such as shaving foam canisters and the like. Suitable dispensers will be well known to those skilled in the art.

The preferred sterilising agent is chlorine dioxide, which may be formed from suitable known reagents. In a preferred embodiment one reagent is a chlorite (notably sodium chlorite) and the other is an acid, preferably with a buffer. Suitable acids include lactic acid, citric acid, boric acid, phosphoric acid, acetic acid, sorbic acid, ascorbic acid, hydrochloric acid or mixtures thereof. In a preferred embodiment a mixture of acids is used, notably a mixture of citric, sorbic and boric acids.

A particularly preferred system is as described in EP 0 785 719, with the corrosion inhibitors optionally not included, and with other additives as desired for particular applications. In addition to suitable indicators, optional additives include foam-promoting agents or stabilisers, humectants, essential oils and fragrances. Other sterilising agents may also be employed; for example chlorine or oxygen. Chlorine may be produced by reaction between a hypochlorite such as sodium hypochlorite, and a suitable acid or buffer. Oxygen may be produced by reaction between a peroxide and a catalyst such as catalase, optionally in the presence of a buffer. For convenience hereinafter, the invention will be described with reference to chlorine dioxide as the sterilising agent.

Suitable foam promoters will be well known to those skilled in the art. Non-limiting examples include: sodium laureth sulphate, ammonium lauryl sulphate, cocamide DEA, cocamidopropyl betaine, sodium lauryl sarcosinate, cocamidopropylamine oxide, monoethanolamine lauryl sulphate, cocamidopropyl hydroxysultaine, cocoyl sarcosinate. Anionic, cationic, non-ionic and amphoteric surfactants may be employed depending on the chemistry of the reagents. The foam promoters are selected to provide a stable foam structure. The foam promoter may comprise from about 0.1 to 50% by weight of the first part, notably from about 1 to 10%, preferably from about 3 to 6%.

Suitable foam stabilisers well known to those skilled in the art may also be used, in proportions similar to those for the foam-promoters. Non-limiting examples include: alkanolamides, for example monoethanolamides and diethanolamides, amine oxides, betaines, protein hydrolysates and cellulose derivatives such as carboxymethylcellulose.

In a preferred embodiment, a humectant is included in at least one of the first and second parts. Humectants serve to reduce the rate of evaporation of components and improve product feel if direct skin contact is involved. We have found that the use of a humectant reduces the volatility of chlorine dioxide, which reduces the odour of chlorine dioxide and prolongs the life of the activated mixture. Non-limiting examples of suitable humectants include sodium lactate and polyols, for example glycerine, sorbitol, propylene glycol, diethylene glycol and ethylene glycol. The humectant may be present in any desired amount, particularly from about 0.1 to 50% by weight, notably from about 0.5 to 10%, preferably from about 1 to 3%.

Where one of the reagents is basic or oxidising, for example sodium chlorite, it is particularly preferred that this reagent is provided in the trigger dispenser rather than in the wipe, because such reagents may react with the fabric over time. Preferably the optional humectant is included in the first part, with the sodium chlorite or other first reagent.

The first and/or second part may further include a biocide to ensure that, in the event of poor mixing of the parts, a biocidal effect is still present. The first and/or second part may also include a preservative.

Equal weights of the first part and the second part may provide, when mixed, a sterilising composition having a pH of from 1.0 to 10.5, but it is preferred that the composition has a pH of from 4.5 to 6.5 as this may result in a more stable compound.

A plurality of fabric members may be provided in a single resealable container, for example a canister with a lid, or a resealable sachet. In a preferred embodiment, each fabric member is provided in its own sachet which may be factory-sealed and disposed of after use. In a particularly preferred embodiment, each sealed sachet contains a single fabric wipe.

Other aspects and benefits of the invention will appear in the following specification, drawings and claims.

BRIEF DESCRIPTION OF THE DRAWINGS

The invention will now be further described, by way of example, with reference to the following drawings in which.

DETAILED DESCRIPTION

Figure 1:
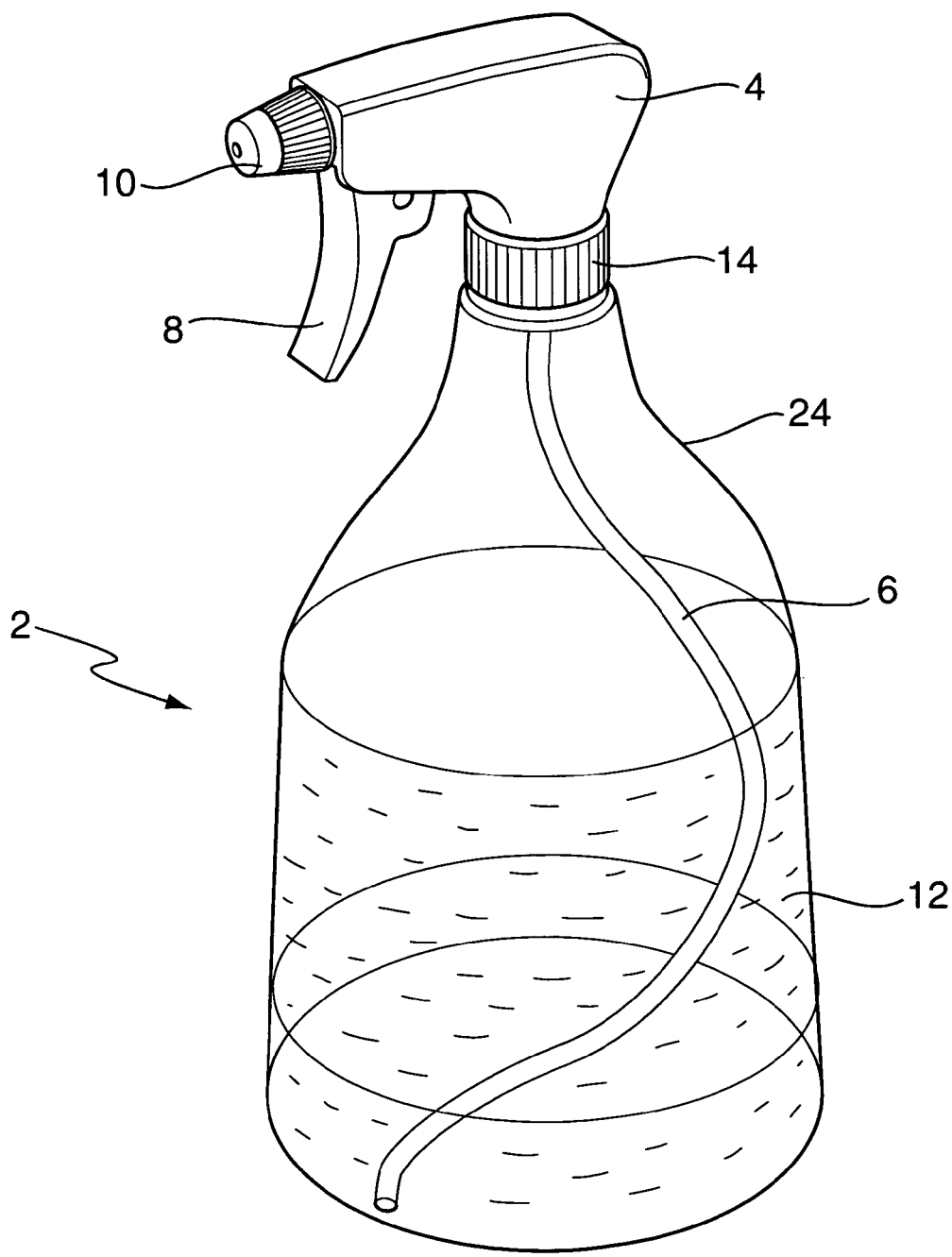
FIG. 1 shows a trigger sprayer for use in a sterilant system in accordance with an embodiment of the present invention.

The trigger sprayer shown in FIG. 1 is of a construction well known per se. The sprayer comprises a body 2 connected to a sprayer head 4 by an internally screw-threaded connector ring 14. A spray nozzle 10 in the head is connected to an aqueous liquid 12 by means of a dip tube 6. A user dispenses the liquid 12 through the nozzle 10 by operation of a trigger 8. Rotation of the nozzle allows the user to dispense the fluid as either a spray of fine droplets or as a foam.

In the present example, the liquid 12 (first part) comprises 0.75% of a first reagent (sodium chlorite), 3.0% foam promoter (Cocamidopropyl Betaine). The remainder is deionised water. In this specification, all parts are by weight unless otherwise indicated. Operation of the trigger 8 dispenses the first part 12 as a foam.

Figure 3:
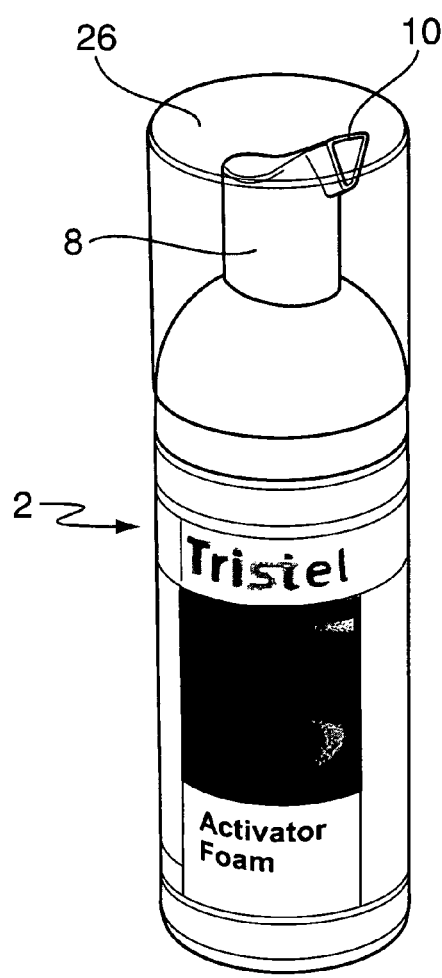
FIG. 3 shows an alternative trigger sprayer for use in a sterilant system in accordance with an alternative embodiment of the invention.

An alternative design of pump dispenser 2 is illustrated in FIG. 3. The trigger 8 is formed integrally with the nozzle 10. Depressing the trigger 8 dispenses a portion of the fluid contents as a foam (referred to as the 'Activator Foam' because it activates the sterilising powers of a sterilising wipe). A protective cap 26 is provided to cover the nozzle 10 and trigger 8 when not in use.

Figure 2:
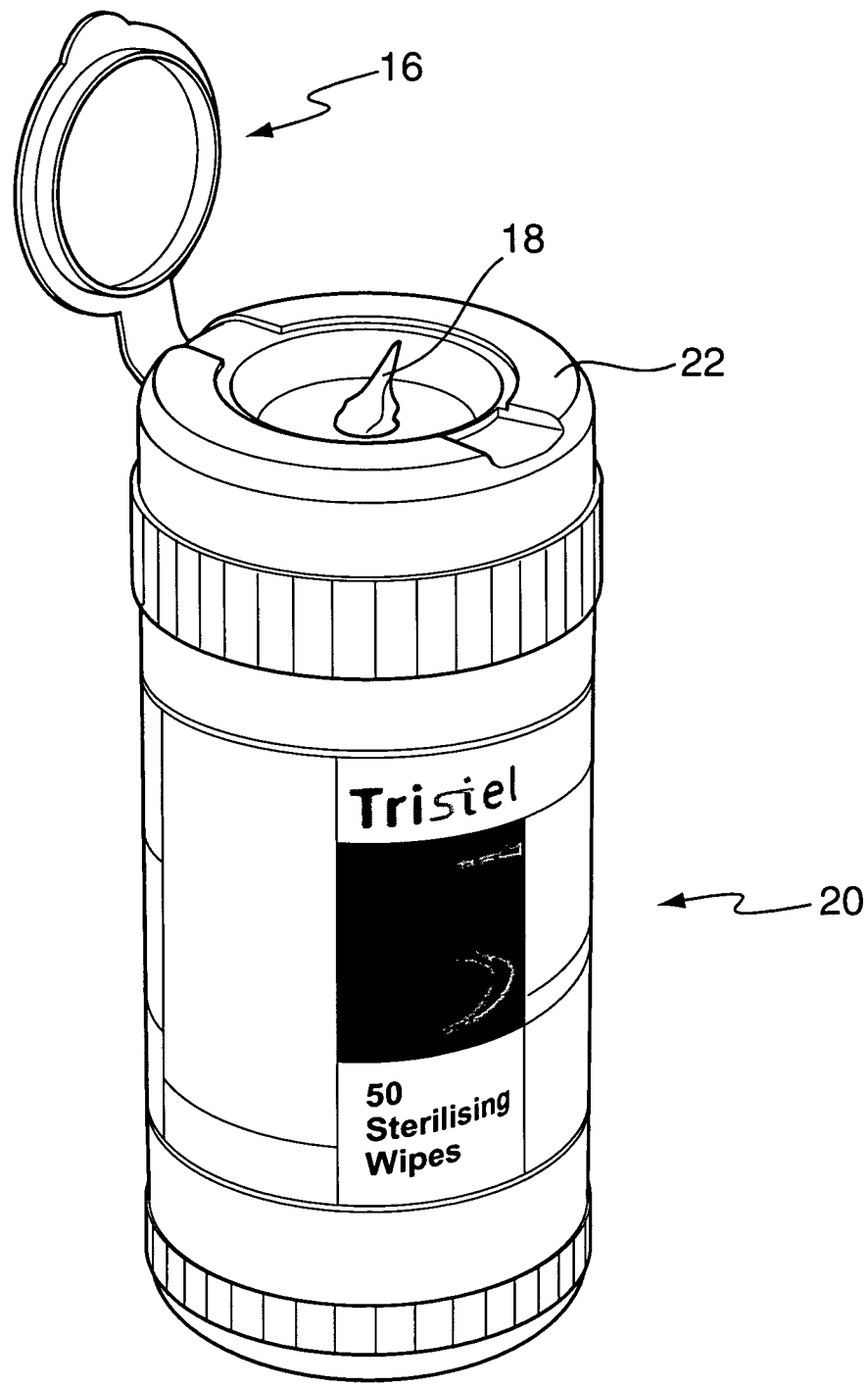
FIGS. 2 and 4 show an canister of sterilising wipes, respectively open and closed, for use in a sterilant system in accordance with an embodiment of the present invention.
Figure 4:
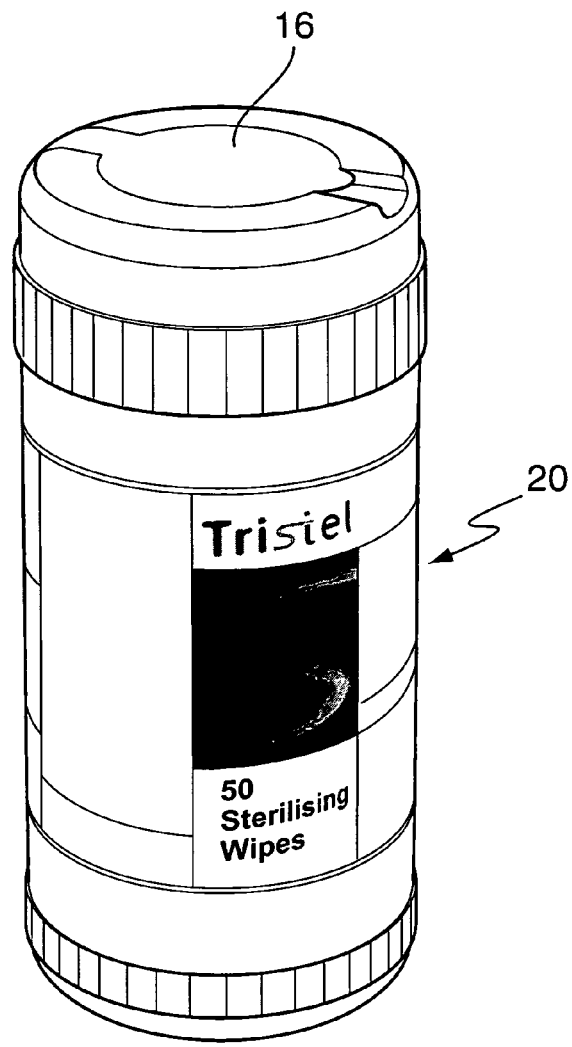

Turning now to FIGS. 2 and 4, a sealable container 20 is also of a construction well known per se. The container 20 is a hollow cylinder fitted with a cap 22. The container 20 contains a roll of interleaved fabric sheets 18. In this example, the fabric sheets 18 are to be used as sterilising wipes, but it will be understood that the sheets 18 could also be used for other applications such as biocidal wound-dressings.

The cap 22 has a central opening through which a tip of the central wipe 18 is disposed. By pulling the central wipe 18, a user may remove this wipe from the container, leaving the next wipe in its place. A stopper 16 is provided on the cap 22 for releasably sealing the container 20.

In this example, the wipes 18 are impregnated with an aqueous acid solution (second part). In this example, the acid solution comprises 0.5% citric acid, 0.05% sorbic acid, 0.05% boric acid. The solution also comprises 0.35% of a buffer (trisodium phosphate). The solution also comprises 0.25% Trisodium Citrate, 1.0% glycerine, 0.1% Benzotriazole, 0.1% Sodium Molybdate and 0.3% Sodium Nitrate. The remainder is deionised water.

The pump dispenser 2 and container 20 together comprise the sterilant system. To prepare a sterilising wipe, a user removes an impregnated wipe 18 from the container 20, and applies a portion of foam from the sprayer 2 to the wipe 18. To facilitate mixing of the reagents in the foam and the wipe, the user may fold the wipe in half and crush or rub the folded wipe before opening it out. Preferably, one of the components is provided with a pH-sensitive indicator which changes colour or becomes coloured when adequate mixing has occurred, thereby indicating that sufficient $ClO_2$ has been generated in the wipe.

Once the sterilising wipe has been prepared, it may be used for a number of applications, including wiping surfaces and sterilising medical equipment such as endoscopes.

Figure 5:
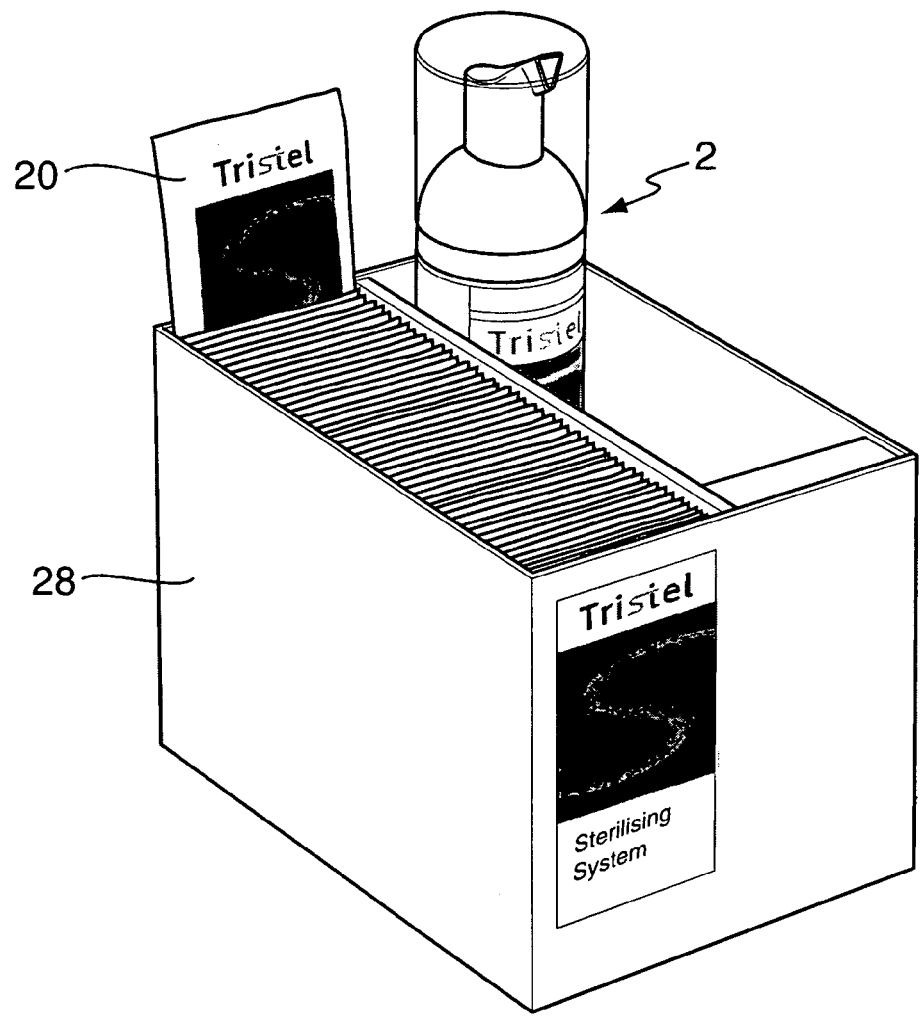
FIG. 5 illustrates a sterilant system in accordance with a further embodiment of the invention.

In the preferred embodiment illustrated in FIG. 5, each sterilising wipe 18 is provided in its own sealed container 20, in this example a sachet. The sterilant system comprises a box 28 of sterilising wipes 18 in individual sachets 20. Each sachet 20 may be factory sealed and may be disposed of after the wipe has been removed. The foam pump dispenser 2 is also provided in the box 28 of sterilising wipe sachets 20.

EXPERIMENTAL RESULTS

Experiment 1

Sterilant wipes in accordance with one embodiment of the invention were tested and compared with conventional wipes saturated with isopropanol (IPA), a general-purpose detergent, and sterile deionised water.

The test method to evaluate effectiveness of the wipes in killing/removing test organisms dried onto test surfaces, involved the following steps.

1. Mark out a six inch (30.5 cm) square test area on the test surface.
2. Inoculate the test surface with 0.5 ml of test organism suspension.
3. Spread the inoculum over the test area using a plastic spreader.
4. Allow the inoculum to dry (about 30 minutes).
5. Don a pair of disposable plastic gloves.
6. Prepare a $ClO_2$ wipe in accordance with the invention, using a prescribed mixing time.
7. Wipe the test area for the prescribed wiping time.
8. Place the wipe in 10 ml of universal neutraliser in a Universal bottle (Test Suspension A). Vortex stir to release organisms.
9. Wipe the entire test area with a cotton-tipped swab (thoroughly/10 times).
10. Dip the swab into 10 ml of universal neutraliser in a Universal bottle after each sampling of the test area and rotate the swab against the inner wall of the bottle to release organisms (Test Suspension B).
11. Prepare 5 serial deci-dilutions of Test Suspension A and Test Suspension B in diluent.
12. Inoculate 0.5 ml of each dilution onto a culture plate and spread using a plastic spreader. Incubate the plates and do a viable count.
13. Calculate $\log_{10}$ reductions achieved from the difference in the initial inoculum and the number of test organisms recovered after disinfection with a $ClO_2$ wipe.

Test variables were as follows.

Test Surface
   A flat stainless steel instrument tray.
Test Organism
   Spores of *Bacillus subtilis* var.niger NCTC 10073 freshly prepared by the method of Beeby & Whitehouse.
Inoculum
   The test surface was inoculated with $1 \times 10^8$ spores.
Suspending Fluid
   Sterile deionised water.
Disinfectant Concentrations
   1. 200 ppm $ClO_2$ (notional)
   2. 300 ppm $ClO_2$ (notional).
Mixing Times
   15+30 seconds.
Wiping Times
   15+30+60 seconds.
Controls
   1. 1% Hospec general purpose neutral liquid detergent (Young's Detergents)/Kimcare Medical Wipes (Kimberly-Clark).
   2. Sterets Alcowipe: 70% IPA (Seton Prebbles Ltd).
   3. Sterile deionised water: Kimcare Medical Wipes (Kimberly-Clark).

Results are given in Table 1.

TABLE 1

| Exp. No. | Disinfectant/ Detergent | Mixing time (seconds) | Wiping time (seconds) | VC Surface | VC Wipe |
|---|---|---|---|---|---|
| 1 | 200 ppm $ClO_2$ | 15 | 15 | 177 | 143 |
| 2 | 200 ppm $ClO_2$ | 15 | 30 | 36 | 14 |
| 3 | 200 ppm $ClO_2$ | 15 | 60 | 10 | 8 |
| 4 | 200 ppm $ClO_2$ | 30 | 15 | 800 | 300 |
| 5 | 200 ppm $ClO_2$ | 30 | 30 | 240 | 27 |
| 6 | 200 ppm $ClO_2$ | 30 | 60 | 29 | 26 |
| 7 | 300 ppm $ClO_2$ | 15 | 15 | 1240 | 330 |
| 8 | 300 ppm $ClO_2$ | 15 | 30 | 530 | 250 |
| 9 | 300 ppm $ClO_2$ | 15 | 60 | 160 | 140 |
| 10 | 300 ppm $ClO_2$ | 30 | 15 | 1450 | 900 |
| 11 | 300 ppm $ClO_2$ | 30 | 30 | 30 | 70 |
| 12 | 300 ppm $ClO_2$ | 30 | 60 | 20 | 10 |
| 13 | 1% Hospec | | 60 | $7.3 \times 10^4$ | $4.3 \times 10^5$ |
| 14 | 70% IPA | | 60 | $1.9 \times 10^4$ | $3.7 \times 10^4$ |
| 15 | Deionised $H_2O$ | | 60 | $2.0 \times 10^5$ | $3.0 \times 10^5$ |

VC = Viable Count

Interpretation of Results
   1. Washing/wiping with water, neutral detergent (1% Hospec), or alcohol (70% IPA) were ineffective 2. For the notional 200 ppm $ClO_2$ wipes the best results were obtained with a mixing time of 15 seconds and a wiping time of 60 seconds.

3. For the notional 300 ppm $ClO_2$ wipes the best results were obtained with a mixing time of 30 seconds and a wiping time of 60 seconds.

4. Results for 200 ppm $ClO_2$ (notional) were surprisingly better than results for 300 ppm (notional), except for mixing times of 30 seconds combined with wiping times of at least 30 seconds.

5. A wiping time of 60 seconds achieved better results than a wiping time of 30 seconds, which in turn achieved better results than a wiping time of 15 seconds.

6. Both $ClO_2$ concentrations achieved good results after a wiping time of 60 seconds. The test surface was inoculated with $1 \times 10^8$ spores. After using the $ClO_2$ wipes, surface counts were reduced to 10 and 29 (200 ppm $ClO_2$) and to 160 and 20 (300 ppm $ClO_2$).

7. A wipe containing 200 or 300 ppm may be useful, as may mixing times of 15 or 30 seconds (or, clearly, any intermediate times). However, it is preferred that wiping times longer than 15 seconds are employed.

These results were obtained using bacterial spores. It is to be expected that a vegetative bacterium such as MRSA will be much more sensitive, so that lower $ClO_2$ concentrations and/or shorter mixing or wiping times may be effective against such bacteria.

Further experiments (2-4) were carried out using 41 gsm spunlace sheets comprised of 50.5% wood pulp and 49.5% PET. The sheets' dimensions were 160 mm×180 mm×0.36 mm. In each experiment the wipes each contained 3 ml of Solution A (formulated as set forth below), made by treating a canister of 50 wipes with 150 ml of Solution A. Each wipe was activated with 1.5 ml of Solution B (formulated as set forth below) from a foam dispenser.

Solution A (Wipe)

Formulation:

|  | Ingredients | Actual % w/w | Tolerance |
|---|---|---|---|
| 1 | Citric acid C.A.S. 77-92-9 | 0.50% | +/−0.60-0.40% |
| 2 | Sorbic acid C.A.S. | 0.005% | +/−0.006-0.004% |
| 3 | Boric acid C.A.S. 10043-35-3 | 0.005% | +/−0.006-0.004% |
| 4 | Trisodium citrate C.A.S. 68-04-02 | 0.25% | +/−0.30-0.20% |
| 5 | Trisodium phosphate C.A.S. 10101-89-0 | 0.35% | +/−0.45-0.25% |
| 6 | Glycerin C.A.S. 56-81-5 | 1.00% | +/−1.10-0.90% |
| 7 | Benzotriazole C.A.S. 95-14-7 | 0.10% | +/−0.15-0.05% |
| 8 | Sodium molybdate C.A.S. 10102-40-6 | 0.10% | +/−0.15-0.05% |
| 9 | Sodium nitrate C.A.S. 7631-99-4 | 0.20% | +/−0.25-0.15% |
| 10 | Preservative (Paramotol) C.A.S. | 0.15% | +/−0.20-0.10% |
| 11 | Deionised water C.A.S. 7732-18-5 | Balance | Balance |

Solution B (Foam)

Formulation:

|  | Ingredients | Actual % w/w | Tolerance |
|---|---|---|---|
| 1 | Sodium chlorite (25% solution) | 0.75% | +/−0.85-0.65% |
| 2 | Cocamidopropyl betaine | 3.00% | +/−3.10-2.90% |
| 3 | Indicator/colour solution (Indicator is cosmetic yellow, No. 5, cl 19140 at 1% solution - 0.6%) | 0.60% | +/−0.07-0.50% |
| 4 | Preservative (Euxyl K 100) | 0.15% | +/−0.20-0.10% |
| 5 | Deionised Water (Purified) C.A.S. 7732-18-5 | 95.50% | +/−Balance |

Experiment 2

A study was carried out to compare the effectiveness of (a) $ClO_2$ wipes in accordance with the invention (b) a 70% IPA wipe (c) a neutral detergent wipe and (d) a water wipe in removing and/or killing (1) *B. subtilis* spores, and (2) *P. aeruginosa* cells dried onto the insertion tube of a flexible endoscope.

Wipes were prepared fresh as required by squirting foam onto a wipe and then scrunching the wipe with the fingers to mix the reagents to form $ClO_2$.

Experiment 2

Test Organisms
*B. subtilis* NCTC 10073 Spores

A suspension containing approximately $10^8$ spores/ml was prepared by the method of Beeby & Whitehouse. A 1 in 10 dilution in sterile distilled water was prepared to produce a suspension containing approximately $10^7$ spores/ml.

*P. aeruginosa* NCTC 6749

A culture containing approximately $10^8$ cells/ml was prepared by inoculating a tube of nutrient broth and incubating for 18 h at 37° C.

Insertion Tube Used in Experiment 2

The insertion tube was 1 meter long, in good condition, withclear markings. The test site used was the 10 cm section between the 30 and 40 markings.

Test Method

1. Immerse a cotton-tipped swab into a suspension of spores or vegetative cells.

2. Inoculate entire surface area of test site with the suspension. Repeat several times. Regarding *B. subtilis* spores, assume that (1) the volume of inoculum=0.1 ml, and (2) the mortality rate on drying out is zero. Hence the viable count of the inoculum=approximately $10^6$ spores. Regarding *P. aeruginosa* cells, assume that (1) the volume of inoculum=0.1 ml, and (2) the mortality rate on drying out is 1 log. Hence the viable count of the inoculum=approximately $10^6$ cells.

3. Place inoculated insertion tube across the top of an empty discard jar with the 10 cm test site resting over the centre of the jar. Allow inoculum to dry out (approximately 30 minutes).

4. Don pair of disposable plastic gloves.

5. Prepare a Wipe: $ClO_2$ (scrunch time=15 sec), IPA, Hospec or water.

6. Wipe test site for the prescribed wipe time (30 sec) as follows: Wrap wipe loosely around the insertion tube and then wipe up and down the test site repeatedly.

7. Place the wipe in 20 ml of universal neutraliser in a Universal bottle. Vortex stir to release recovered spores/cells (Test Suspension A).

8. Swab entire test site with a cotton-tipped swab. Dip swab into 10 ml of universal neutraliser in a Universal bottle and rotate swab against the inner wall of the bottle to release recovered spores/cells. Repeat 10 times then break off cotton-tip of swab and leave in the neutraliser. Vortex stir to release recovered spores/cells (Test Suspension B).

9. Prepare 5 serial deci-dilutions of Test Suspension A and Test Suspension B in diluent.

10. Inoculate 0.5 ml of each dilution onto a culture plate and spread using a plastic spreader. Incubate plates. Viable count.

11. Calculate $\log_{10}$ reductions achieved from the difference in the number of spores or cells inoculated onto the test site (approximately $10^6$) and the number recovered after cleaning and/or disinfection.

Wipes Used in Experiment 2

1. $ClO_2$ Wipe (scrunch time=15 seconds).
2. 70% IPA wipe: Azowipe (Vernon Carus).
3. Hospec wipe: Kimberley Clark Medical Wipe immersed in 1% Hospec and then squeezed to remove excess solution.
4. Water wipe: Kimberley Clark Medical Wipe immersed in sterile water and then squeezed to remove excess water.

Experiment 2—Results

TABLE 2

| Exp | Test organism | Disinfectant/ detergent | Scrunch time (sec) | Wipe time (sec) | Viable Count (0.5 ml) | |
|---|---|---|---|---|---|---|
| | | | | | Surface | Wipe |
| 1 | B. subtilis | $ClO_2$ | 15 | 30 | 0 | 0 |
| 2 | | $ClO_2$ (repeat) | 15 | 30 | 0 | 0 |
| 3 | | 70% IPA | | 30 | $5.0 \times 10^2$ | $2.7 \times 10^3$ |
| 4 | | 1% Hospec | | 30 | $1.5 \times 10^2$ | $2.6 \times 10^3$ |
| 5 | | Water | | 30 | $3.0 \times 10^1$ | $2.5 \times 10^3$ |
| 6 | P. aeruginosa | $ClO_2$ | 15 | 30 | 0 | 0 |
| 7 | | $ClO_2$ (repeat) | 15 | 30 | 0 | 0 |
| 8 | | 70% IPA | | 30 | 2 | 0 |
| 9 | | 1% Hospec | | 30 | $6.2 \times 10^3$ | $8.0 \times 10^4$ |
| 10 | | Water | | 30 | $2.5 \times 10^4$ | $1.5 \times 10^5$ |

TABLE 3

| Exp | Test organism | Disinfectant/ detergent | Total spores/cells recovered | |
|---|---|---|---|---|
| | | | Surface[1] | Wipe[2] |
| 1 | B. subtilis | $ClO_2$ | 0 | 0 |
| 2 | | $ClO_2$ (repeat) | 0 | 0 |
| 3 | | 70% IPA | $1.0 \times 10^4$ | $1.0 \times 10^5$ |
| 4 | | 1% Hospec | $3.0 \times 10^3$ | $1.0 \times 10^5$ |
| 5 | | Water | $6.0 \times 10^2$ | $1.0 \times 10^5$ |
| 6 | P. aeruginosa | $ClO_2$ | 0 | 0 |
| 7 | | $ClO_2$ (repeat) | 0 | 0 |
| 8 | | 70% IPA | $4.0 \times 10^1$ | 0 |
| 9 | | 1% Hospec | $1.2 \times 10^5$ | $3.2 \times 10^6$ |
| 10 | | Water | $5.0 \times 10^5$ | $6.0 \times 10^6$ |

[1]Viable count in Table 1 × 20 (0.5 ml of 10 ml neutraliser plated out).
[2]Viable count in Table 1 × 40 (0.5 ml of 20 ml neutraliser plated out).

Experiment 2—Conclusions

1. $ClO_2$ wipes were completely effective against both B. subtilis spores and P. aeruginosa cells. No spores or cells were recovered in duplicate experiments.

2. IPA wipes exhibited good activity against P. aeruginosa cells but did not eliminate all of the test cells—40 viable cells were recovered from the test site on the insertion tube.

3. IPA wipes were ineffective against B. subtilis spores. IPA proved less effective than 1% Hospec or water which may be attributable to the coagulant properties of alcohol (fixing spores on the test site).

4. Wipes saturated with 1% Hospec were ineffective against either B. subtilis spores or P. aeruginosa cells.

5. Wipes saturated with water were ineffective against either B. subtilis spores or P. aeruginosa cells.

Experiment 3

Evaluation of the Effectiveness of $ClO_2$ Wipes in Killing/Removing Methicillin Resistant Staphylococcus Aureus (MRSA) Dried onto a Stainless Steel Test Surface Test Method The following test method was used to evaluate the effectiveness of $ClO_2$ Wipes in killing/removing test-organisms dried onto test surfaces. The test method involves the following steps:

1. Mark out an 18 inch (457.2 mm) square on the test surface.

2. Inoculate test surface with 4.5 ml of test organism suspension.

3. Spread inoculum over 18 inch (457.2 mm) square test area using a plastic spreader.

4. Allow inoculum to dry (30-60 minutes).

5. Don pair of disposable plastic gloves.

6. Prepare a $ClO_2$ Wipe using the prescribed scrunch time (15 seconds).

7. Wipe test area for the prescribed wipe time (30 seconds).

8. Place the $ClO_2$ Wipe in 20 ml of universal neutraliser in a universal bottle. Vortex stir to release organisms. (Test Suspension A).

9. Swab entire test area with a cotton-tipped swab. Dip swab into 10 ml of universal neutraliser in a universal bottle and rotate cotton-tip against the inner wall of the bottle to release organisms. Repeat 10 times. Finally, snap off cotton-tip into the neutraliser. Vortex stir to release organisms. (Test Suspension B).

10. Prepare 5 serial deci-dilutions of Test Suspension A and Test Suspension B in diluent.

11. Inoculate 0.5 ml of each dilution onto a culture plate and spread using a plastic spreader. Incubate plates. Viable count.

12. Calculate $\log_{10}$ reductions achieved from the difference in the initial inoculum and the number of test organisms recovered after cleaning/disinfection with a ClO2 Wipe.

13. Repeat above using control wipes (70% IPA, 1% Hospec & sterile water).
Variables Selected in Experiment 3
Test Surface
  A flat stainless steel laboratory bench.
Test Organism
  Methicillin Resistant *Staphylococcus aureus* (MRSA): a clinical isolate from the Royal Preston Hospital.
Inoculum
  The test surface was inoculated with >$10^9$ bacterial cells: 4.5 ml of an overnight culture in Nutrient Broth.
Suspending Fluid
  Nutrient Broth
Scrunch Time
  15 seconds
Wipe time
  30 seconds
Controls
  1. 70% IPA wipe: Azowipe (Vernon Carus).
  2. 1% Hospec general purpose neutral liquid detergent (Young's Detergents)/Kimcare Medical Wipe (Kimberly-Clark). The wipe was immersed in 1% Hospec and then squeezed with the fingers to remove excess fluid.
  3. Sterile deionised water/Kimcare Medical Wipe (Kimberly-Clark). The wipe was immersed in water and then squeezed with the fingers to remove excess fluid.
Results

TABLE 4

| Exp | Disinfectant/detergent | Mixing time (sec) | Wiping time (sec) | Viable Count Surface | Viable Count Wipe |
|---|---|---|---|---|---|
| 1 | ClO$_2$ | 15 | 30 | 0 | 0 |
| 2 | ClO$_2$ (repeat) | 15 | 30 | 0 | 0 |
| 3 | 70% IPA | | 30 | $5.5 \times 10^4$ | 9 |
| 4 | 1% Hospec | | 30 | $5.5 \times 10^4$ | $6.0 \times 10^4$ |
| 5 | Deionised H$_2$O | | 30 | $5.7 \times 10^4$ | $5.9 \times 10^4$ |

TABLE 5

| Exp | Disinfectant/detergent | Mixing time (sec) | Wiping time (sec) | Total number of organisms recovered Surface[1] | Total number of organisms recovered Wipe[2] |
|---|---|---|---|---|---|
| 1 | ClO$_2$ | 15 | 30 | 0 | 0 |
| 2 | ClO$_2$ (repeat) | 15 | 30 | 0 | 0 |
| 3 | 70% IPA | | 30 | $1.1 \times 10^6$ | $3.6 \times 10^2$ |
| 4 | 1% Hospec | | 30 | $1.1 \times 10^6$ | $2.4 \times 10^6$ |
| 5 | Deionised H$_2$O | | 30 | $1.1 \times 10^6$ | $2.4 \times 10^6$ |

[1]Viable Count in Table 1 × 20 (0.5 ml of 10 ml neutraliser plated out).
[2]Viable Count in Table 1 × 40 (0.5 ml of 20 ml neutraliser plated out).

Interpretation of Results
  1. Wiping with a ClO$_2$ Wipe for 30 seconds was completely effective. No test organisms were recovered from either the test surface or the wipes in duplicate experiments.
  2. Wiping the test surface with a 70% IPA wipe (Azowipe) for 30 seconds was ineffective. This could be due to:
    (a) an exposure time of 30 seconds was not long enough to kill the MRSA
    (b) the IPA evaporated off the test surface before the minimum exposure time required to kill the MRSA
    (c) the volume of IPA on the wipe was insufficient to deal with the >$10^9$ MRSA dried onto the 18 inch test surface
    (d) a combination of the above.
  3. Only 360 test organisms were recovered from the Azowipe. This could be due to:
    (a) entrapment of test organisms in the fibres
    (b) incomplete/slow neutralisation of the residual IPA on the wipe by the neutraliser
    (c) a combination of the above
  4. Wipes saturated with either 1% Hospec or sterile water were ineffective.

Experiment 4

This experiment was carried out to evaluate the effectiveness of ClO$_2$ Wipes in killing/removing spores of *Bacillus subtilis* var. *niger* NCTC 10073 dried out for 24 h at room temperature on a stainless steel test surface.
Test Method
  1. Mark out a 12 inch (304.8 mm) square on the test surface.
  2. Inoculate test surface with 1.0 ml of aqueous spore suspension.
  3. Spread inoculum over 12 inch (304.8 mm) square test area using a plastic spreader.
  4. Allow inoculum to dry out naturally at room temperature for 24 h.
  5. Don pair of disposable plastic gloves.
  6. Prepare a ClO$_2$ Wipe using the prescribed scrunch time (15 seconds).
  7. Wipe test area for the prescribed wipe time (30 seconds).
  8. Place the ClO$_2$ Wipe in 20 ml of universal neutraliser in a universal bottle. Vortex stir to release organisms. (Test Suspension A).
  9. Swab entire test area with a cotton-tipped swab. Dip swab into 10 ml of universal neutraliser in a universal bottle and rotate cotton-tip against the inner wall of the bottle to release organisms. Repeat 10 times. Finally, snap off cotton-tip into the neutraliser. Vortex stir to release organisms. (Test Suspension B).
  10. Prepare 5 serial deci-dilutions of Test Suspension A and Test Suspension B in diluent.
  11. Inoculate 0.5 ml of each dilution onto a culture plate and spread using a plastic spreader.
  12. Repeat above using a control wipe (a Medical Wipe saturated with sterile water).
  13. Incubate plates. Viable count.
  14. Calculate $\log_{10}$ reductions achieved using the ClO2 Wipe from the difference in viable count obtained using the ClO2 Wipe and the control wipe.
Variables Selected in Experiment 4
Test Surface
  A flat stainless steel instrument tray.
Test Organism
  *Bacillus subtilis* var. *niger* NCTC 10073. A spore suspension was prepared by the method of Beeby & Whitehouse.
Inoculum
  The test surface was inoculated with (a) $10^6$ spores, and (b) $10^8$ spores.
Suspending Fluid
  Deionised water.
Drying Time
  The inoculated instrument tray was allowed to dry out naturally at room temperature for 24 h in a dark cupboard.
Scrunch Time
  15 seconds.
Wipe Time
  30 seconds.

Control

1. Sterile deionised water/Kimcare Medical Wipe (Kimberly-Clark). The wipe was immersed in water and then squeezed with the fingers to remove excess fluid.

Results

TABLE 6

| Exp. | Inoculum (spores) | Disinfectant/ detergent | Mixing time (sec) | Wiping time (sec) | Viable Count Surface | Viable Count Wipe |
|---|---|---|---|---|---|---|
| 1 | $10^6$ | $ClO_2$ | 15 | 30 | 0 | 0 |
| 2 | $10^6$ | Water | 15 | 30 | $2.0 \times 10^2$ | $2.1 \times 10^2$ |
| 3 | $10^8$ | $ClO_2$ | 15 | 30 | $4.8 \times 10^2$ | $1.3 \times 10^2$ |
| 4 | $10^8$ | Water | 15 | 30 | $6.6 \times 10^4$ | $1.9 \times 10^5$ |

TABLE 7

| Exp. | Inoculum (spores) | Disinfectant/ detergent | Mixing time (sec) | Wipe time (sec) | Total number of spores recovered Surface[1] | Total number of spores recovered Wipe[2] |
|---|---|---|---|---|---|---|
| 1 | $10^6$ | $ClO_2$ | 15 | 30 | 0 | 0 |
| 2 | $10^6$ | Water | 15 | 30 | $4.0 \times 10^3$ | $8.4 \times 10^3$ |
| 3 | $10^8$ | $ClO_2$ | 15 | 30 | $9.6 \times 10^3$ | $5.2 \times 10^3$ |
| 4 | $10^8$ | Water | 15 | 30 | $1.3 \times 10^6$ | $7.6 \times 10^6$ |

[1]Viable Count in Table 1 × 20 (0.5 ml of 10 ml neutraliser plated out).
[2]Viable Count in Table 1 × 40 (0.5 ml of 20 ml neutraliser plated out).

Interpretation of Results

1. Spores dried out for 24 h at room temperature on a stainless steel test surface were not easy to dislodge using a Medical Wipe saturated with deionised water. With the $10^6$ inoculum the recovery was 4.0-8.4×$10^3$ spores leaving 2-3 $\log_{10}$ spores on the surface (assuming no mortality). With the $10^8$ inoculum the recovery was 1.3-7.6×$10^6$ spores leaving 1-2 $\log_{10}$ spores on the surface.

2. $ClO_2$ Wipes were effective in killing/removing spores dried out for 24 h at room temperature on the stainless steel test surface. With the $10^6$ inoculum, no spores were recovered from either the surface or wipe which represents a 3-4 $\log_{10}$ reduction on both the surface and wipe. With the $10^8$ inoculum, a 2-3 $\log_{10}$ reduction of spores was achieved on the surface and a 3-4 $\log_{10}$ reduction on the wipe.

Thus, the invention provides a sterilant system which can be prepared in situ and which provides bactericidal, fungicidal, virucidal, and sporicidal fabrics. The system is particularly useful for sterilising wipes and for the dressing of wounds and ulcers.

To promote and accelerate the production of $ClO_2$ from the solutions we have found that acetic anhydride and ascorbic acid may advantageously be employed together as additives in Solution A. A preferred concentration for each additive is 0.4%

It is appreciated that certain features of the invention which are, for clarity, described in the context of separate embodiments, may also be provided in combination in a single embodiment. Conversely, various features of the invention which are, for brevity, described in the context of a single embodiment, may also be provided separately, or in any suitable combination. It is to be recognized that various alterations, modifications, and/or additions may be introduced into the constructions and arrangements of parts described above without departing from the spirit and scope of the present invention. As used herein, the indefinite articles 'a' and 'an' connote 'one or more' unless the context requires otherwise.

I claim:

1. A two-part sterilant system comprising:
   (a) a first part comprising a first reagent in a carrier medium; and
   (b) a second part which is miscible with the first part and which comprises a second reagent in a carrier medium;
   wherein the first reagent and the second reagent will react when mixed to provide a sterilising composition;
   wherein the first part is a fluid which includes a foam promoter and is contained in a trigger-operated foam dispenser constructed for dispensing the first part as foam;
   wherein the second part is absorbed or impregnated in at least one fabric wipe containing an aqueous fluid in a sealed container; and
   wherein the first part or the second part further includes a humectant for reducing evaporation of components in the sterilising composition, said humectant being present in an amount from 0.1 to 50% w/w of said first part or said second part.

2. A sterilant system according to claim 1, wherein the at least one fabric wipe comprises a plurality of fabric wipes, each of which is provided in its own separate sealed sachet.

3. A sterilant system according to claim 1, wherein at least one of the first part and the second part includes an indicator reagent that changes colour when the parts are mixed together.

4. A sterilant system according to claim 3, wherein the first part and the second part have a different pH and wherein the indicator reagent changes colour in response to a change in pH when the parts are mixed.

5. A sterilant system according to claim 1, wherein one of the first part and the second part comprises a solution containing sodium chlorite or sodium chlorate and the other comprises an acidic solution.

6. A sterilant system according to claim 5, wherein the acidic solution comprises a solution of citric acid, sorbic acid and boric acid.

7. A sterilant system according to claim 1, wherein the foam promoter is present in an amount from 0.1 to 50% w/w of said first part.

8. A sterilant system according to claim 7, wherein said foam promoter is present in an amount from 3 to 6% w/w of said first part.

9. A sterilant system according to claim 1, wherein said humectant is present in an amount from 1 to 3% w/w of said first part or said second part.

10. A sterilant system according to claim 1, wherein when equal weights of the first part and the second part are mixed they provide a sterilising composition having a pH of from 4.5 to 6.5.

11. A sterilant system according to claim 5, wherein the first part comprises said solution of sodium chlorite or sodium chlorate.

12. A sterilant system according to claim 11, wherein said first part comprises a solution of sodium chlorite and said acidic solution comprises an aqueous mixture of citric acid, sorbic acid, boric acid, and a buffer.

13. A sterilant system according to claim 1, wherein one of the first reagent and the second reagent comprises chlorite and the other comprises hypochlorite.

14. A sterilant system according to claim 1, wherein one of the first reagent and the second reagent comprises chlorate and the other comprises a peroxide and an acid.

15. A two-part sterilant system comprising:
(a) a first part comprising a first reagent in a carrier medium; and
(b) a second part which is miscible with the first part and which comprises a second reagent in a carrier medium;
wherein the first reagent and the second reagent will react when mixed to provide a sterilising composition;
wherein the first part is a gel and is contained in a trigger-operated dispenser constructed for dispensing the first part as a gel;
wherein the second part is absorbed or impregnated in at least one fabric wipe containing an aqueous fluid in a sealed container; and
wherein the first part or the second part further includes a humectant for reducing evaporation of components in the sterilising composition, said humectant being present in an amount from 0.1 to 50% w/w of said first part or said second part.

16. A two-part wound-dressing system comprising:
(a) a first part comprising a first reagent in a carrier medium; and
(b) a second part which is miscible with the first part and which comprises a second reagent in a carrier medium;
wherein the first reagent and the second reagent will react when mixed to provide a sterilising composition;
wherein the first part is a fluid which includes a foam promoter and is contained in a trigger-operated foam dispenser constructed for dispensing the first part as a foam;
wherein the second part is absorbed or impregnated in at least one fabric wound dressing containing an aqueous fluid in a sealed container; and
wherein the first part or the second part further includes a humectant for reducing evaporation of components in the sterilising composition, said humectant being present in an amount from 0.1 to 50% w/w of said first part or said second part.

17. A wound-dressing system according to claim 16, wherein the at least one fabric wound dressing comprises a plurality of fabric wound dressings, each of which is provided in its own separate sealed sachet.

18. A two-part wound-dressing system comprising:
(a) a first part comprising a first reagent in a carrier medium; and
(b) a second part which is miscible with the first part and which comprises a second reagent in a carrier medium;
wherein the first reagent and the second reagent will react when mixed to provide a sterilising composition;
wherein the first part is contained in a pump dispenser constructed for dispensing the first part as a gel;
wherein the second part is absorbed or impregnated in at least one fabric wound dressing containing an aqueous fluid in a sealed container; and
wherein the first part or the second part further includes a humectant for reducing evaporation of components in the sterilising composition, said humectant being present in an amount from 0.1 to 50% w/w of said first part or said second part.

19. A sterilant system according to claim 15, wherein the at least one fabric wipe comprises a plurality of fabric wipes, each of which is provided in its own separate sealed sachet.

20. A sterilant system according to claim 1, wherein the at least one fabric wipe comprises a plurality of fabric wipes interleaved in a resealable container.

21. A sterilant system according to claim 15 wherein the at least one fabric wipe comprises a plurality of fabric wipes interleaved in a resealable container.

22. A wound-dressing system according to claim 16, wherein the at least one fabric wound dressing comprises a plurality of fabric wound dressings interleaved in a resealable container.

23. A wound-dressing system according to claim 18, wherein the at least one fabric wound dressing comprises a plurality of fabric wound dressings, each of which is provided in its own separate sealed sachet.

24. A wound-dressing system according to claim 18, wherein the at least one fabric wound dressing comprises a plurality of fabric wound dressings interleaved in a resealable container.

* * * * *